United States Patent
Du

(10) Patent No.: US 10,194,930 B2
(45) Date of Patent: Feb. 5, 2019

(54) EXTRACORPOREAL SHOCK WAVE LITHOTRIPTER AND CHARGING AND DISCHARGING CIRCUIT FOR EXTRACORPOREAL SHOCK WAVE LITHOTRIPTER

(71) Applicant: SUZHOU XIXIN MEDICAL INSTRUMENTS CO., LTD., Suzhou, Jiangsu (CN)

(72) Inventor: Xixin Du, Suzhou (CN)

(73) Assignee: SUZHOU XIXIN MEDICAL INSTRUMENTS CO., LTD., Suzhou (CN)

( * ) Notice: Subject to any disclaimer, the term of this patent is extended or adjusted under 35 U.S.C. 154(b) by 344 days.

(21) Appl. No.: 15/033,360

(22) PCT Filed: Jul. 4, 2014

(86) PCT No.: PCT/CN2014/081702
§ 371 (c)(1),
(2) Date: Apr. 29, 2016

(87) PCT Pub. No.: WO2015/062306
PCT Pub. Date: May 7, 2015

(65) Prior Publication Data
US 2016/0262778 A1    Sep. 15, 2016

(30) Foreign Application Priority Data
Nov. 1, 2013   (CN) .......................... 2013 1 0534492

(51) Int. Cl.
*A61B 17/225* (2006.01)
*A61H 23/00* (2006.01)
(Continued)

(52) U.S. Cl.
CPC ......... *A61B 17/225* (2013.01); *A61H 23/008* (2013.01); *A61B 2017/00159* (2013.01);
(Continued)

(58) Field of Classification Search
CPC ........ A61B 17/225; A61B 2017/00181; A61B 2017/00159; A61H 23/008; A61H 2201/1207; G10K 15/06
(Continued)

(56) References Cited

U.S. PATENT DOCUMENTS

| 4,796,608 A | * | 1/1989 | Koehler | ................... G10K 9/12 601/4 |
| 5,658,239 A | * | 8/1997 | Delmenico | ........ A61B 17/2256 601/4 |

(Continued)

FOREIGN PATENT DOCUMENTS

| CN | 1206583 A | 2/1999 |
| CN | 2403368 Y | 11/2000 |

(Continued)

OTHER PUBLICATIONS

Han, Ming. "Principle of Extracorporeal Shock Wave Lithotripter and its Localizing". China Medical Equipment, No. 9, vol. 8, Sep. 30, 2011, p. 74, col. 1, the third paragraph from the bottom, to p. 75, col. 1, the first paragraph, and figure 1.

(Continued)

*Primary Examiner* — Sanjay Cattungal
(74) *Attorney, Agent, or Firm* — Oliff PLC

(57) ABSTRACT

An extracorporeal shock wave lithotripter and a charging and discharging circuit for an extracorporeal shock wave lithotripter are disclosed. The charging circuit is formed by a resistor and a capacitor, and the discharging circuit is formed by the capacitor, a high-voltage switch and a shock wave source apparatus. The capacitance of the capacitor is 1.5 µF~2.5 µF, the pressure peak value of the focus of shock waves generated by discharging to the shock wave source apparatus by the capacitor is 6 Mpa~30 MPa, a positive pressure period of the bottom pulse width is 3 µs and a negative pressure period is 5 µs.

10 Claims, 3 Drawing Sheets

(51) Int. Cl.
   *G10K 15/06* (2006.01)
   *A61B 17/00* (2006.01)
(52) U.S. Cl.
   CPC .............. *A61B 2017/00181* (2013.01); *A61H 2201/1207* (2013.01); *G10K 15/06* (2013.01)
(58) Field of Classification Search
   USPC .......................................... 600/439; 601/1–3
   See application file for complete search history.

(56) References Cited

U.S. PATENT DOCUMENTS

| | | | | |
|---|---|---|---|---|
| 6,298,264 | B1* | 10/2001 | Zhong | A61B 17/22 |
| | | | | 604/20 |
| 2005/0038361 | A1* | 2/2005 | Zhong | A61B 17/225 |
| | | | | 601/4 |
| 2007/0232964 | A1* | 10/2007 | Voss | A61H 23/008 |
| | | | | 601/4 |

FOREIGN PATENT DOCUMENTS

| | | |
|---|---|---|
| CN | 103536339 A | 1/2014 |
| CN | 203524735 U | 4/2014 |
| WO | 2009/128061 A2 | 10/2009 |

OTHER PUBLICATIONS

Chen, Jingqiu et al. "Studies on Mechanical Mechanism About Stone Comminution and Tissue Trauma in Extra-Corporeal Shock Wave Lithotripsy". Advances in Mechanics, No. 4, vol. 37, Nov. 25, 2007, p. 593, col. 1, the third paragraph from the bottom, and figure 4.

Sep. 29, 2014 International Search Report issued in International Patent Application No. PCT/CN2014/081702.

* cited by examiner a) b) c) d) e)

EXTRACORPOREAL SHOCK WAVE LITHOTRIPTER AND CHARGING AND DISCHARGING CIRCUIT FOR EXTRACORPOREAL SHOCK WAVE LITHOTRIPTER

TECHNICAL FIELD

The present invention relates to medical apparatus and instrument field, in particularly, to an extracorporeal shock wave lithotripter and a charging and discharging circuit for an extracorporeal shock wave lithotripter.

BACKGROUND TECHNOLOGY

With the development of medical technology, the extracorporeal shock wave lithotripter is used increasingly. In order to break up intracorporal calculus more thoroughly, the focus pressure of shock wave is designed to be higher and higher. However, it brings about that the pressure of the shock wave exceeds the tolerance limit of human soft tissues resulting in damages of human soft tissues. Therefore, the problem which is urgent to be solved is to provide an extracorporeal shock wave lithotripter which has little or almost no damage to human body.

SUMMARY

The present invention is intended to provided an extracorporeal shock wave lithotripter which can break up intracorporal calculus, and meanwhile which can reduce or avoid damages to human soft tissues.

Based on the above purposes, the present invention on one aspect provides an extracorporeal shock wave lithotripter comprising a shock wave generation apparatus which has a charging and discharging circuit. The charging circuit is formed by a resistor and a capacitor, and the discharging circuit is formed by successively connecting the capacitor, a high-voltage switch and a shock wave source apparatus in series, the capacitance of the capacitor is 1.5 µF-2.5 µF. The pressure peak value of the focus of shock waves generated by discharging to the shock wave source apparatus by the capacitor is 6 Mpa-20 MPa, and the bottom pulse width of the shock waves is 3 µs-5 µs. The bottom pulse width of the shock waves is specifically preferred to be that a positive pressure period is 3 µs and a negative pressure period is 5 µs.

Preferably, the charging voltage of the charging circuit is 5000V-11000V.

Preferably, the capacitance of the capacitor is 1.6 µF-2.4 µF.

Preferably, the shock wave source apparatus is any one of an electromagnetic wave source, an electrohydraulic wave source and a piezoelectric wave source.

In a specific embodiment, the shock wave source apparatus preferably is an electromagnetic wave source comprising a coil of which one end is connected with the capacitor and the other end is connected with the high-voltage switch, a metal diaphragm arranged opposite to the coil, and an insulating layer arranged between the coil and the metal diaphragm, wherein, the coil and the metal diaphragm serve as an entirety which is sealed and placed in an inner cavity of a rubber bag filled with water.

More specifically, the coil is a spherical single-layer spiral coil, the number of turns of the coil is 15-30, and the diameter of the coil is 65 mm-130 mm. The coil man be windingly formed by copper wire, and the cross section of the copper wire is a circle shape with a diameter of 0.5 mm-2.5 mm, or a rectangle shape with a length of 0.5 mm-2.5 mm and a width of 0.5 mm-1.5 mm. The metal diaphragm may employ a fine copper diaphragm with a thickness of 0.1 mm-0.3 mm. The fine copper diaphragm mentioned here and everywhere else refers to that the copper content is best to be over 99.99%.

Preferably, the shock waves have a positive pressure period and a negative pressure period, the breaking direction of calculus caused by the positive pressure period and the breaking direction of calculus caused by the negative pressure period are perpendicular to each other.

The present invention on another aspect provides a charging and discharging circuit applied in the above-mentioned extracorporeal shock wave lithotripter, comprising a charging circuit and a discharging circuit. Wherein, the charging circuit is formed by a resistor and a capacitor, and the discharging circuit is formed by the capacitor, a high-voltage switch and a shock wave source apparatus, the capacitance of the capacitor which is both a constituted element of the charging circuit and a constituted element of the discharging circuit is 1.5 µF-2.5 µF.

In a preferable instance, the capacitance is 1.6 µF-2.4 µF.

On the basis of the above technical schemes, the beneficial effects of the present invention are as follow:

the present invention selects and uses a capacitor of 1.5 µF-2.5 µF to cause the pressure peak value of the focus of the generated shock waves to be 6 Mpa-30 MPa and the bottom pulse width of the shock waves to be 3 µs-5 µs. Due to that the pressure of the shock wave is small, the head of curve is smooth, most of the shock wave penetrates into the calculus, stress concentration is induced when encountering impurities, and the length of the wave width (i.e. the duration of the shock wave) is long, an irreversible and accumulated central breakage of the calculus model is caused. And the pressure of the shock wave is low and most of the shock wave penetrates into the calculus, as a result a reflected pressure generated by the outer surface of the calculus model also is low, and therefore the damage to human soft tissues is greatly reduced. Meanwhile, the pressure and pressure differential of the shock waves is very low, which can generate a very small cavitation effect that is not enough to cause damages to organism.

DETAILED DESCRIPTION OF EMBODIMENTS

In the following, the technical schemes in the embodiments of the present invention are explained clearly and fully combining with the accompanying drawings, and apparently, the described embodiments are merely a part of the embodiments of the present invention, not all of the embodiments. Based on the embodiments of the present invention, all other embodiments obtained by one of ordinary skill in the art without creative work belong to the scope protected by the present invention.

Figure 1:
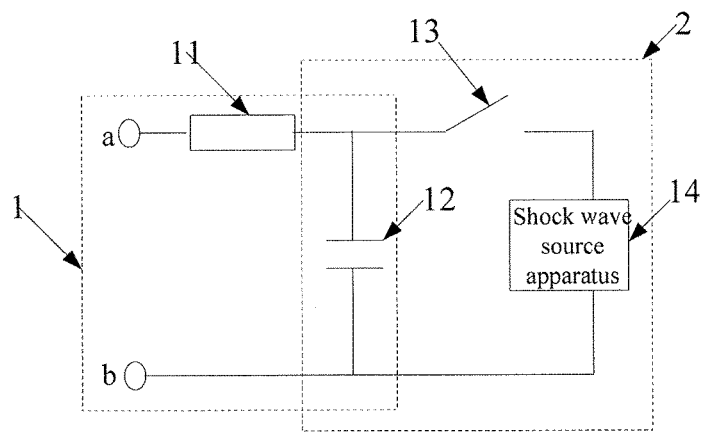
FIG. 1 is a structure schematic diagram of a shock wave generation apparatus of the present invention.

Extracorporeal shock wave lithotripters all need a shock wave generation apparatus. The extracorporeal shock wave generation apparatus comprises a charging and discharging circuit. FIG. 1 shows the charging and discharging circuit. Specifically, it comprises a charging circuit 1 and a discharging circuit 2, wherein the charging circuit 1 is formed by a resistor 11 and a capacitor 12, and the discharging circuit 2 is formed by successively connecting the capacitor 12, a high-voltage switch 13 and a shock wave source apparatus 14 in series. Firstly, the capacitor 12 is charged, and after charging completed, the high-voltage switch 13 is switched on, the capacitor 12 instantaneously discharges to the shock wave source apparatus 14 resulting the shock wave. Wherein, there are two discharging modes, one of which is manual discharging, that is, pressing the switch 13 one time and discharging is carried out one time. The other mode is continuous discharging, that is, discharging in a given frequency. The discharging frequency may be set as required, for example, 30 times per minute.

At present, the shock wave source apparatus 14 has three common types of wave sources, the electromagnetic wave source, the electrohydraulic wave source and the piezoelectric wave source. For more clearly describing the present invention, a self-focusing electromagnetic shock wave generation apparatus is taken as an example to introduce the present invention in detail.

Figure 2:
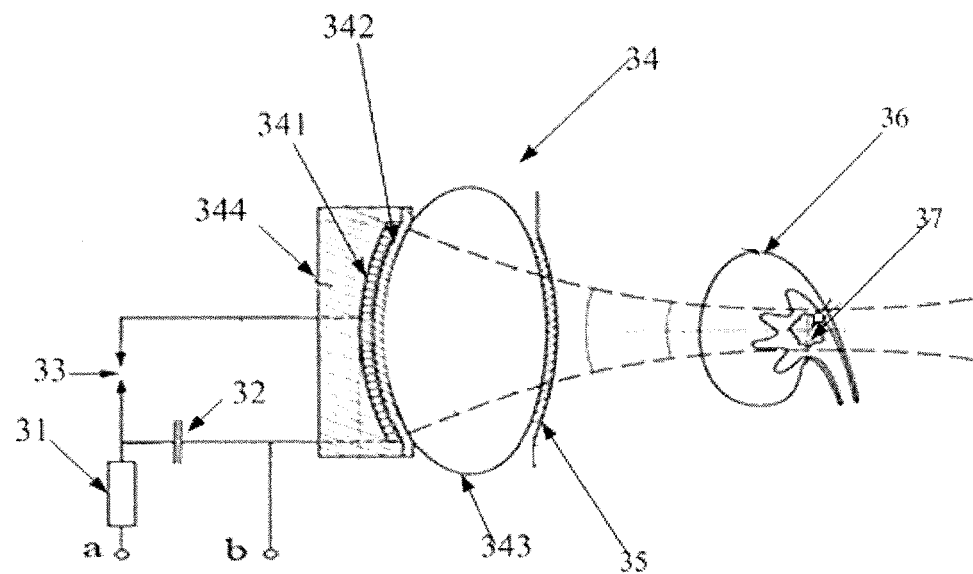
FIG. 2 is a structure schematic diagram of a self-focusing electromagnetic shock wave generation apparatus of the present invention.

FIG. 2 is a schematic diagram of employing a self-focusing electromagnetic shock wave generation apparatus to treat calculus 37 in human kidney 36. The self-focusing electromagnetic shock wave generation apparatus specifically comprises a charging circuit and a discharging circuit, wherein the charging circuit is formed by a resistor 31 and a capacitor 32; the discharging circuit is formed by successively connecting the capacitor 32, a high-voltage switch 33 and a electromagnetic shock wave source apparatus 34 in series. Wherein, the electromagnetic shock wave source apparatus 34 comprises a coil 341 of which one end is connected with the capacitor 32 and the other end is connected with the high-voltage switch 33, a metal diaphragm 342 arranged opposite to the coil 341, a rubber bag 343 filled with water inside, and an liner 344 connected with the rubber bag 343. The coil 341 and the metal diaphragm 342 are arranged inside the inner cavity of the rubber bag 343, and an insulating lay (not shown in the figure) is arranged between the coil 341 and the metal diaphragm 342, which are already known to the person in the art and hence no longer described herein. The capacitor 32 is connected to the coil 341 via a conductive wire, and the rubber bag 343 is tightly attached to human skin 35. The coil 341 preferably is a spherical single-layer spiral coil and windingly formed by copper wire, the metal diaphragm 342 may select a copper diaphragm.

Figure 3:
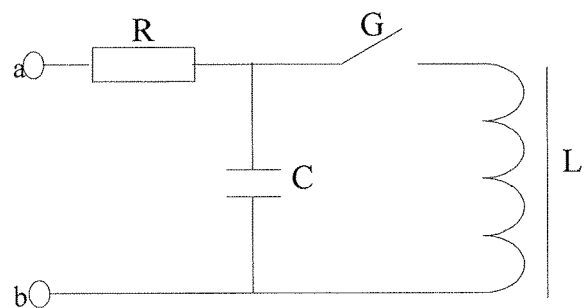
FIG. 3 is a structure equivalent diagram of a discharging circuit of the present invention.

In FIG. 3, the charging and discharging circuit of the self-focusing electromagnetic wave source is shown in a manner of equivalent circuit diagram of a circuit formed by a capacitor C, a resistor R, a high-voltage switch G and an inductor L, wherein the inductor L is essentially obtained by inducing from the coil 341 by the metal diaphragm 342. The charging voltage in the present invention may be obtained form an alternating voltage transformed by a high-voltage transformer and then rectified by a rectifier.

The working principle of the self-focusing electromagnetic wave source is that, the capacitor C is charged to a given voltage, one discharge is completed through the high-voltage switch G by the capacitor C to generate a powerful pulse current in the coil which generates an induced current when flowing through the coil 341, and the two magnetic fields formed by the two currents repel each other causing the generation of a brief and rapid movement of the metal diaphragm 342 such that a strong pressure pulse is actuated in the water and spreads to form a shock wave.

Figure 4:
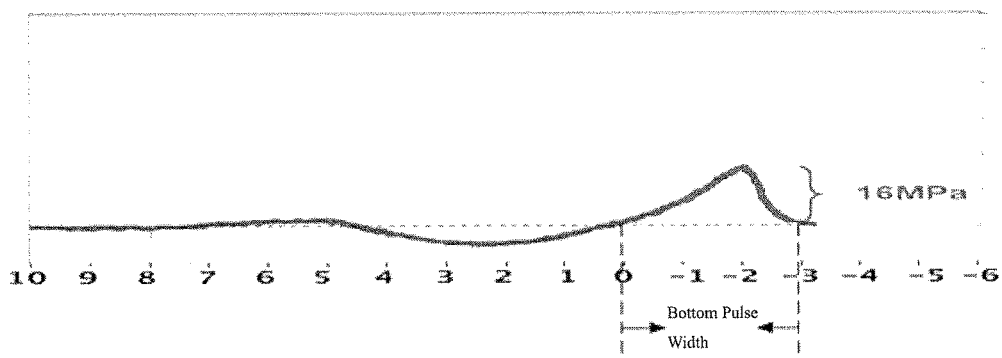
FIG. 4 is a waveform graph of the focal region shock wave generated by an extracorporeal shock wave lithotripter of the present invention.

The existing extracorporeal shock wave lithotripter has a relatively large damage to human body, and the damage is mainly derived from the pressure peak value of the focus of the shock wave generated by the existing lithotripter is too large, and the frequency thereof is high. In order to decrease the damage on human body, it is required to reduce the pressure and frequency of the shock wave. In the extracorporeal shock wave lithotripter, the pressure peak value of the focus of the shock wave is determined by the capacitance value, the charging voltage and the electrical energy transformation capability of the shock wave source apparatus, and the frequency of the shock wave is mainly determined by the capacitance value. On this basis, the applicant had multiple experiments and finally obtained and demonstrated that an extracorporeal shock wave lithotripter which can reduce the voltage required by breaking stone and can well complete the breakage, and meanwhile has especially small side effects. This is achieved by utilizing an approach of increasing the capacitance which is specifically as follow: the capacitance of the capacitor C employed by the extracorporeal shock wave lithotripter is 1.5 μF-2.5 μF. Most preferably, the capacitance of the capacitor is 1.6 μF-2.4 μF. By means of the capacitor discharging to generate the shock wave, the pressure peak value of the focus of the shock waves generated by the lithotripter of the present invention is 6 Mpa-20 MPa, in which the bottom pulse width has, for example, a positive pressure period of 3 μs and a negative pressure period of 5 μF. The wave form thereof is shown in FIG. 4.

According to formula $W=\frac{1}{2}CU^2$, it can be known that, the energy discharged by the capacitor is co-determined by both the capacitance and the charging voltage, and the mechanical energy finally transformed from electrical energy also depends on the electrical energy transformation capability of the shock wave source apparatus. Therefore, the person in the art may select an appropriate charging voltage according to different electrical energy transformation capabilities of the shock wave source apparatuses. In a specific embodiment of the present invention, the charging voltage may range from 5000V to 11000V.

When employing the above-mentioned self-focusing electromagnetic wave source, and taking the service life and effect into account, the number of turns of the coil is 15-30, the diameter of the coil is 65 mm-130 mm, and the coil 341 is windingly formed by copper wire, and may be chosen to be a copper wire with a cross section of a circle shape or a rectangle shape. When selecting a copper wire with a cross section of a circle shape, the diameter ranges from 0.5 mm to 2.5 mm. When selecting a copper wire with a cross section of a rectangle shape, the length of the rectangle shape is 0.5 mm-2.5 mm and the width is 0.5 mm-1.5 mm, preferably, the rectangle shape has a length of about 2 mm and a width of about 1 mm. The metal diaphragm 342 is a pure copper diaphragm with a thickness of 0.1 mm-0.3 mm.

We know that, the existing extracorporeal shock wave lithotripters depend on a high pressure to instantaneously break the calculus in human body. While the pressure peak value of the focus of the shock waves generated by the extracorporeal shock wave lithotripter of the present invention is 6 Mpa-20 MPa which is smaller than the pressure peak value of the focus of the shock waves generated by the existing extracorporeal shock wave lithotripter, it was found by experiment that this pressure also can achieve an ideal breaking effect on the same experimental calculus. Taking a capacitance of 1.5 µF-2.5 µF and a pressure peak value of the focus of 16 MPa as example, a calculus breakage may be achieved through about 644 times of discharging. The mechanism and effect of the extracorporeal shock wave lithotripter of the present invention depending on low pressure to break stone are explained as follow.

Figure 5:
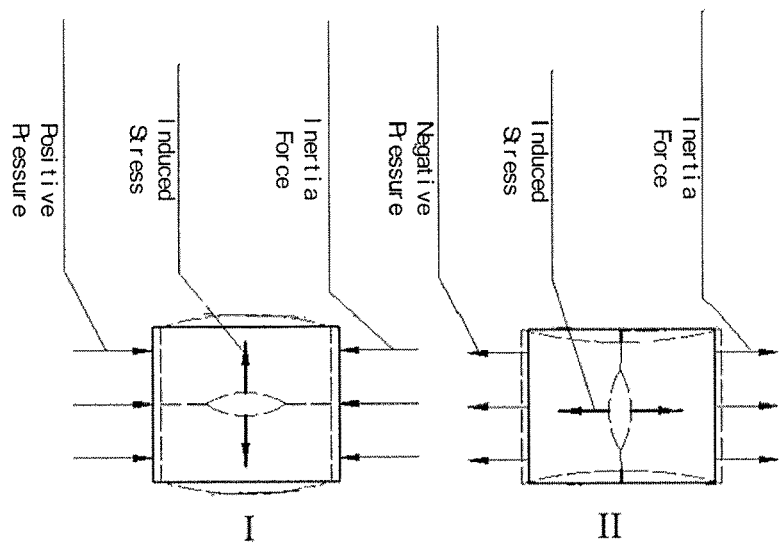
FIG. 5 is a schematic diagram of continuous encounters of the shock waves generated by an extracorporeal shock wave lithotripter of the present invention and the calculus at the focus.

FIG. 4 is a specific waveform of the shock wave generated by the extracorporeal shock wave lithotripter of the present invention, the pressure peak value of the focus being about 16 MPa, and the bottom pulse width of a positive pressure period being 3 µs, and the bottom pulse width of a negative pressure period being 5 µs. FIG. 5 shows the situations when encounters of the shock waves shown in FIG. 4 and the calculus happen. The ordinate axis in FIG. 4 represents the pressure value of the shock wave in MPa, and the abscissa axis is time in µs.

With regard to the shock wave shown in FIG. 4, due to its small focus pressure peak value, wide bottom pulse width, and relatively smooth head portion, that is, low frequency, most energy of it penetrates into the calculus when it encounters calculus (as shown in FIG. 4), and high stress concentration is induced when it encounters an impurity, a small defect and a micro fracture inside calculus, which is an amplified induced stress, resulting in that the original impurity or fracture continuously extends under the action of this stress, and turns into an irreversible accumulation breakage; repeating multiple times according to this way, the calculus being beaten suddenly crumbles when its fatigue limit equals to or is smaller than the pressure (negative pressure) it bears. And due to the relatively wider bottom pulse width of the shock wave generated by the present invention, that is, increasing the time span, the accumulation breakage is more obvious. As repeating the discharging time and time again, the micro fracture gradually enlarges, and the calculus crumbles when the accumulation is up to a certain extent. This is a different breakage mechanism, and we call it center fragmentation effect. The stress here always is tensile stress which is perpendicular to or parallel to the movement direction of the shock wave.

The shock wave shown in FIG. 4 consists of a positive pressure period I and a negative pressure period II, and FIG. 5 shows the fragmentation conditions of calculus at the positive pressure period I and the negative pressure period II. Wherein the movement direction of the shock wave of the positive pressure period I is parallel to the resulted fragmentation direction of the calculus, and the movement direction of the shock wave of the negative pressure period II is perpendicular to the resulted fragmentation direction of the calculus. That is to say, the fragmentation direction of the calculus induced by the shock wave of the positive pressure period I and the fragmentation direction of the calculus induced by the shock wave of the negative pressure period II is perpendicular to each other. The surface of fracture of the calculus is certainly on the section where the induced stress is fully larger than the breakage stress at the earliest to induce the breakage of the calculus.

Figure 6:
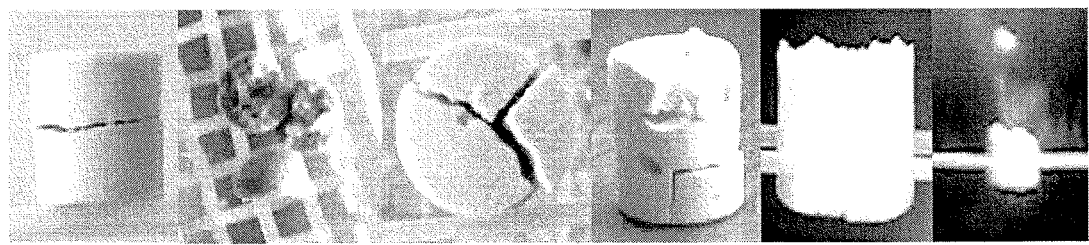
FIG. 6 is a diagram reflecting the relationship between the pressure of the shock wave and the breakage of the calculus.

During experiment, according to the pressure, different fragmentation model can be steadily achieved under different pressure. The experiment proved that, the fragmentation models constantly varied as the pressure changed from low to high, for example, from 6 MPa to 30 Mpa. When the pressure of the focus equals to 7 Mpa, double fragmentation appears. When the pressure increases to 9.5 Mpa, triple fragmentation appears. When the pressure increases to 17 Mpa, multiple fragmentation appears. When the pressure increases to 23 Mpa, mixed fragmentation appears. When the pressure increases to 29.5 Mpa, pure shock fragmentation appears. FIG. 6 shows several pictures reflecting the relationship between the pressure and the fragmentation, and the fragmentation model is different when the pressure of the focus is different, which is shown in FIG. 6.

Due to that the shock wave shown in FIG. 4 has a small focus pressure peak value, and due to that most energy of it penetrates into the calculus when it encounters calculus, the increased pressure due to reflecting is very little, the pressure around the periphery of the calculus is very small, the cavitation effect is also very little, there is almost no side effect to adjacent soft tissues.

The above specific embodiments further detailed illustrate the purposes, technical schemes and advantages of the present invention, and it should be noted that the above are only specific embodiments of the present invention, those skilled in the art can present invention, various modifications and variations can be made by the person in the art without departing from the spirit and scope of the invention. Thus, the present invention is also intended to encompass those changes and modifications of the present invention which belong to the scope of the claims of the invention and equivalents thereof.

The invention claimed is:

1. An extracorporeal shock wave lithotripter, comprising:
a shock wave generation apparatus comprising:
a charging circuit formed by a resistor and a capacitor, a capacitance of the capacitor being 1.5 µF-2.5 µF; and
a discharging circuit formed by successively connecting the capacitor, a high-voltage switch, and an electromagnetic wave source in series, shock waves with a pressure peak value of a focus of 6 Mpa-30 MPa being generated by discharging to the electromagnetic wave source by the capacitor through the high-voltage switch, and a bottom pulse width of the shock waves being 3 µs-5 µs, the electromagnetic wave source comprising:
a spherical single-layer spiral coil of which one end is connected with the capacitor and the other end is connected with the high-voltage switch, a number of turns of the spherical single-layer spiral coil being 15-30, a diameter of the spherical single-layer spiral coil being 65 mm-130 mm, and the spherical single-layer spiral coil being windingly formed by copper wire, a cross section of the copper wire being a circle shape with a diameter of 0.5 mm-2.5 mm, or a rectangle shape with a length of 0.5 mm-2.5 mm and a width of 0.5 mm-1.5 mm;
a copper diaphragm arranged opposite to the spherical single-layer spiral coil, the copper diaphragm having a thickness of 0.1 mm-0.3 mm; and
an insulating layer arranged between the spherical single-layer spiral coil and the copper diaphragm, the spherical single-layer spiral coil and the copper diaphragm serving as a unit which is sealed and then placed in an inner cavity of a rubber bag filled with water.

2. The extracorporeal shock wave lithotripter according to claim 1, wherein a charging voltage of the charging circuit is 5000V-11000V.

3. The extracorporeal shock wave lithotripter according to claim 1, wherein the capacitance of the capacitor is 1.6 µF-2.4 µF.

4. The extracorporeal shock wave lithotripter according to claim 1, wherein the capacitance of the capacitor is 2.0 µF-2.3 µF.

5. The extracorporeal shock wave lithotripter according to claim 1, wherein the shock waves have a positive pressure period and a negative pressure period, and a breaking direction of calculus caused by the positive pressure period and a breaking direction of calculus caused by the negative pressure period are perpendicular to each other.

6. A charging and discharging circuit for use in an extracorporeal shock wave lithotripter, comprising:
   a charging circuit formed by a resistor and a capacitor, a capacitance of the capacitor being 1.5 µF-2.5 µF; and
   a discharging circuit formed by successively connecting the capacitor, a high-voltage switch, and an electromagnetic wave source in series, shock waves with a pressure peak value of a focus of 6 Mpa-30 MPa being generated by discharging to the electromagnetic wave source by the capacitor through the high-voltage switch, and a bottom pulse width of the shock waves being 3 µs-5 µs, the electromagnetic wave source comprising:
      a spherical single-layer spiral coil of which one end is connected with the capacitor and the other end is connected with the high-voltage switch, a number of turns of the spherical single-layer spiral coil being 15-30, a diameter of the spherical single-layer spiral coil being 65 mm-130 mm, and the spherical single-layer spiral coil being windingly formed by copper wire, a cross section of the copper wire being a circle shape with a diameter of 0.5 mm-2.5 mm, or a rectangle shape with a length of 0.5 mm-2.5 mm and a width of 0.5 mm-1.5 mm;
      a copper diaphragm arranged opposite to the spherical single-layer spiral coil, the copper diaphragm having a thickness of 0.1 mm-0.3 mm; and
      an insulating layer arranged between the spherical single-layer spiral coil and the copper diaphragm, the spherical single-layer spiral coil and the copper diaphragm serving as a unit which is sealed and then placed in an inner cavity of a rubber bag filled with water.

7. The charging and discharging circuit according to claim 6, wherein a charging voltage of the charging circuit is 5000V-11000V.

8. The charging and discharging circuit according to claim 6, wherein the capacitance of the capacitor is 1.6 µF-2.4 µF.

9. The charging and discharging circuit according to claim 6, wherein the capacitance of the capacitor is 2.0 µF-2.3 µF.

10. The charging and discharging circuit according to claim 6, wherein the shock waves have a positive pressure period and a negative pressure period, and a breaking direction of calculus caused by the positive pressure period and a breaking direction of calculus caused by the negative pressure period are perpendicular to each other.

* * * * *